(12) United States Patent
Flett et al.

(10) Patent No.: US 10,548,667 B2
(45) Date of Patent: Feb. 4, 2020

(54) SYSTEM AND METHOD FOR PATIENT IMPLANT ALIGNMENT

(71) Applicant: Corin Limited, Gloucestershire (GB)

(72) Inventors: Magnus Flett, Gloucestershire (GB); Stefano Alfonsi, Gloucestershire (GB)

(73) Assignee: Corin Limited, Gloucestershire (GB)

( * ) Notice: Subject to any disclaimer, the term of this patent is extended or adjusted under 35 U.S.C. 154(b) by 0 days.

(21) Appl. No.: 14/995,223

(22) Filed: Jan. 14, 2016

(65) Prior Publication Data
US 2016/0206379 A1 Jul. 21, 2016

(30) Foreign Application Priority Data
Jan. 15, 2015 (GB) .................................. 1500647.1

(51) Int. Cl.
A61B 34/10 (2016.01)
A61B 90/00 (2016.01)

(52) U.S. Cl.
CPC ............ *A61B 34/10* (2016.02); *A61B 90/361* (2016.02); *A61B 2034/108* (2016.02)

(58) Field of Classification Search
None
See application file for complete search history.

(56) References Cited

U.S. PATENT DOCUMENTS

| 6,304,768 | B1 * | 10/2001 | Blume | A61B 34/73 600/407 |
| 6,470,207 | B1 * | 10/2002 | Simon | A61B 34/20 378/207 |
| 7,203,277 | B2 * | 4/2007 | Birkenbach | A61B 6/032 378/205 |
| 7,239,330 | B2 * | 7/2007 | Sauer | G06T 19/003 345/633 |
| 7,605,826 | B2 * | 10/2009 | Sauer | G06F 3/04815 345/630 |
| 8,565,853 | B2 * | 10/2013 | Frigg | G06F 19/3437 600/407 |
| 8,585,598 | B2 * | 11/2013 | Razzaque | A61B 8/4245 600/411 |

(Continued)

FOREIGN PATENT DOCUMENTS

| WO | 2004001569 | 12/2003 |
| WO | 2005087125 | 9/2005 |
| WO | 2008079546 | 7/2008 |

OTHER PUBLICATIONS

Great Britain Search Report dated Sep. 18, 2015 for application No. GB1500647.1.

*Primary Examiner* — Motilewa Good Johnson
(74) *Attorney, Agent, or Firm* — A.C. Entis-IP Ltd.; Allan C. Entis; Kenichi N. Hartman

(57) ABSTRACT

A method for aligning a patient implant, the method comprising the steps of: generating a digital implant model of the patient implant; determining a desired alignment of the patient implant based on predetermined alignment data; imaging an operative area of the patient to create patient-specific implant reference data; creating a virtual overlay of the digital implant model in the determined desired alignment relative to the patient-specific implant reference data; and operatively aligning the patient implant using the virtual overlay. A patient implant system to implement the method is also provided.

19 Claims, 7 Drawing Sheets

(56) References Cited

U.S. PATENT DOCUMENTS

| | | | |
|---|---|---|---|
| 8,876,830 B2* | 11/2014 | Hodorek | A61B 17/155 606/87 |
| 8,922,589 B2* | 12/2014 | Laor | G06T 19/006 345/633 |
| 9,248,000 B2* | 2/2016 | Sarvestani | A61B 34/20 |
| 9,251,721 B2* | 2/2016 | Lampotang | G09B 23/285 |
| 9,721,389 B2* | 8/2017 | Holmquist | G06T 19/006 |
| 9,767,608 B2* | 9/2017 | Lee | A61B 1/00045 |
| 2002/0140694 A1* | 10/2002 | Sauer | G06T 19/003 345/419 |
| 2003/0210812 A1* | 11/2003 | Khamene | A61B 90/36 382/128 |
| 2004/0238732 A1* | 12/2004 | State | G02B 27/017 250/250 |
| 2005/0085714 A1* | 4/2005 | Foley | A61B 34/20 600/424 |
| 2005/0182320 A1* | 8/2005 | Stifter | A61B 5/103 600/429 |
| 2005/0203380 A1* | 9/2005 | Sauer | G02B 7/002 600/417 |
| 2006/0015030 A1* | 1/2006 | Poulin | A61B 90/36 600/424 |
| 2008/0118115 A1 | 5/2008 | Williamson | |
| 2008/0269596 A1* | 10/2008 | Revie | G06Q 10/087 600/424 |
| 2009/0088830 A1* | 4/2009 | Mohamed | A61F 2/91 623/1.11 |
| 2010/0210939 A1* | 8/2010 | Hartmann | A61B 5/062 600/424 |
| 2011/0029093 A1* | 2/2011 | Bojarski | A61F 2/389 623/20.35 |
| 2011/0159451 A1* | 6/2011 | Kuo | A61C 7/002 433/24 |
| 2012/0157887 A1* | 6/2012 | Fanson | A61F 2/32 600/595 |
| 2012/0209394 A1* | 8/2012 | Bojarski | A61F 2/30942 623/20.32 |
| 2013/0172731 A1* | 7/2013 | Gole | A61B 5/0035 600/424 |
| 2013/0324839 A1* | 12/2013 | Chien | A61B 6/12 600/424 |
| 2014/0135744 A1* | 5/2014 | Stein | A61B 17/00 606/1 |
| 2015/0046818 A1* | 2/2015 | Wade | A61B 19/56 715/719 |
| 2015/0138168 A1* | 5/2015 | Nagano | G06F 3/0383 345/179 |
| 2015/0138186 A1* | 5/2015 | Carrell | F24C 15/2021 345/419 |
| 2015/0257846 A1* | 9/2015 | Kubiak | A61B 6/487 600/407 |
| 2016/0125603 A1* | 5/2016 | Tanji | A61B 17/152 382/131 |
| 2016/0143699 A1* | 5/2016 | Tanji | A61B 34/20 600/431 |

* cited by examiner

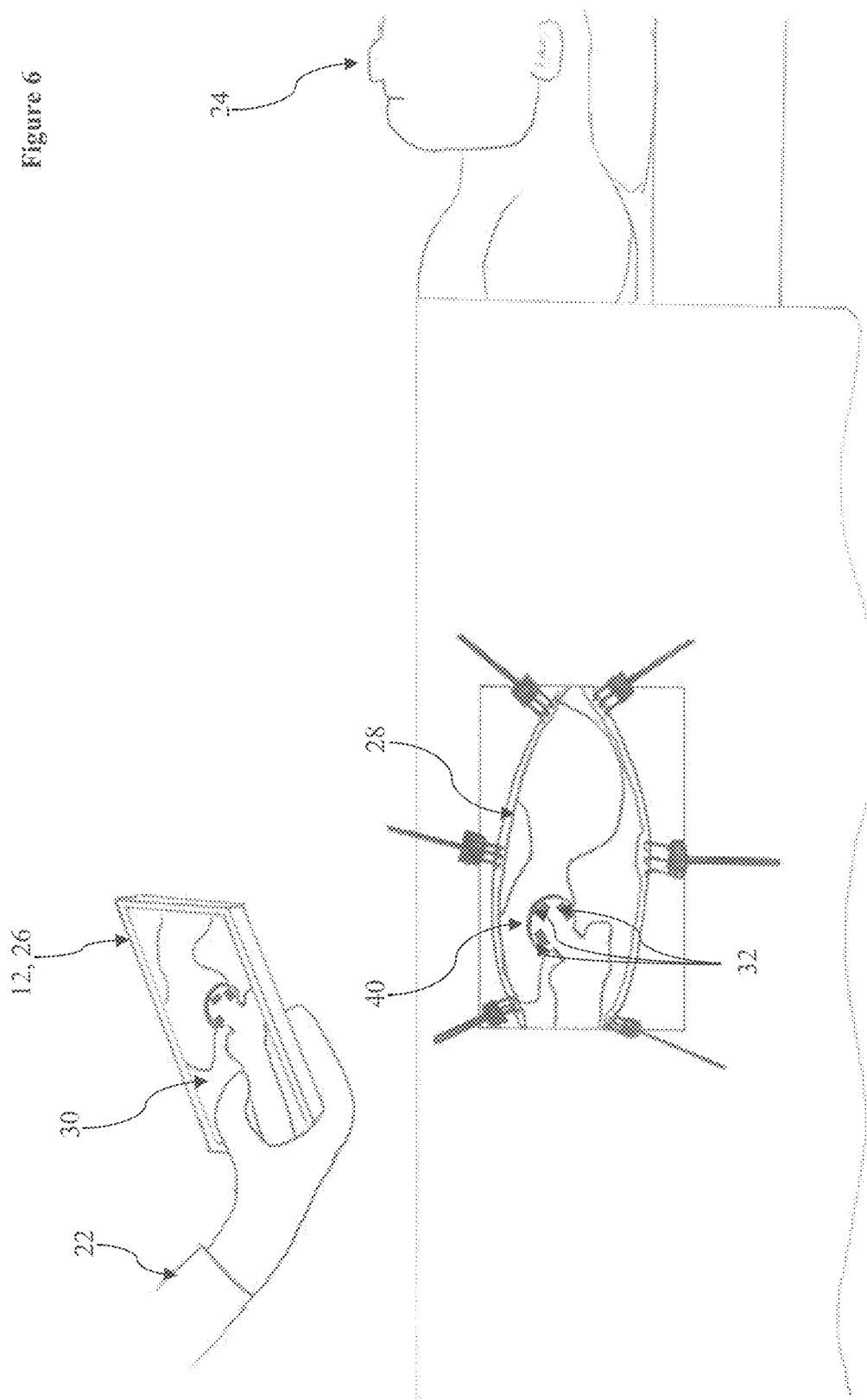

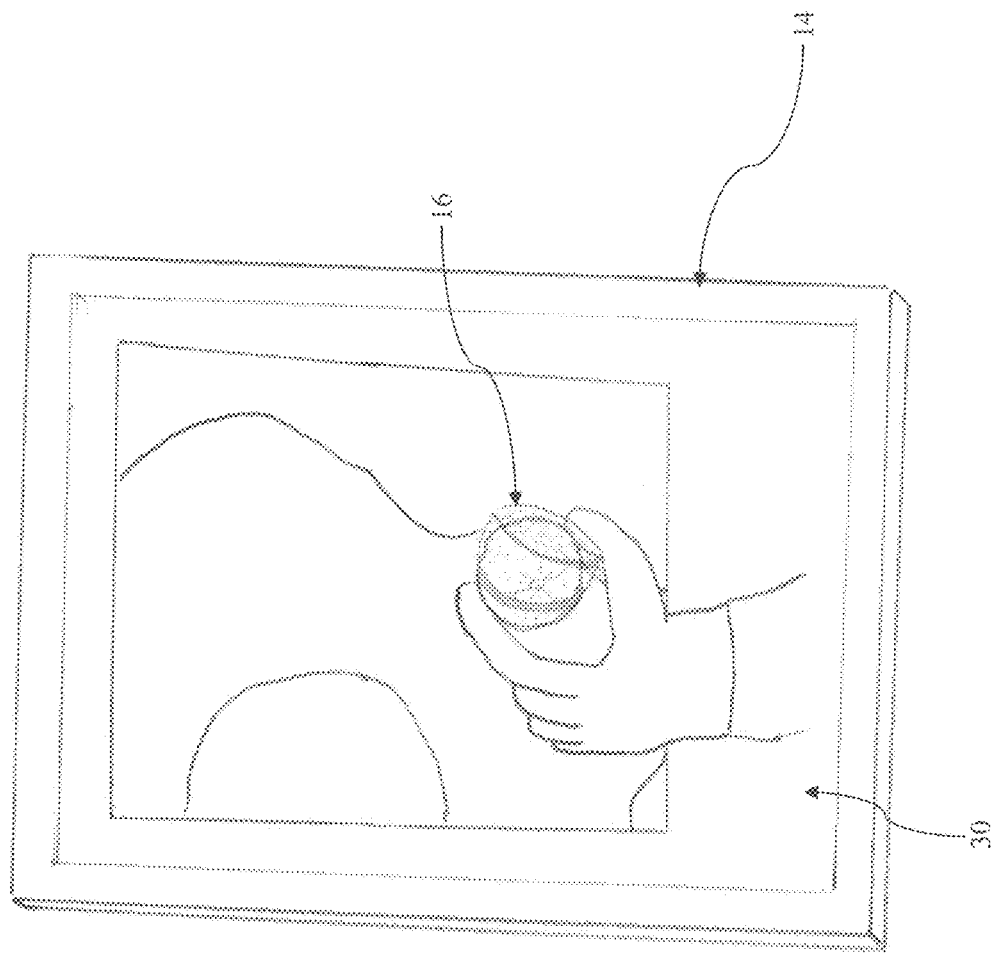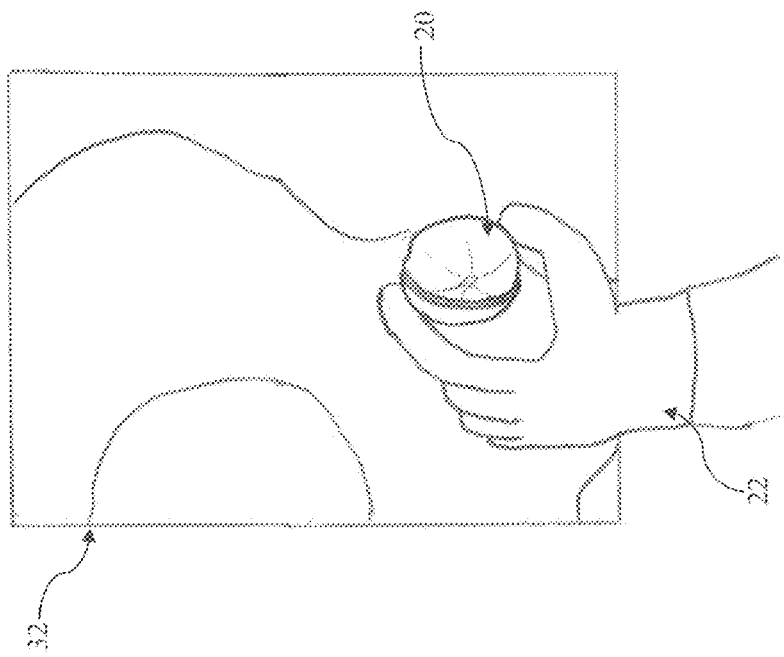

SYSTEM AND METHOD FOR PATIENT IMPLANT ALIGNMENT

RELATED APPLICATIONS

This application claims the benefit under 35 U.S.C. § 119(a)-(d) of British Patent Application No. 1500647.1 filed on Jan. 15, 2015, the disclosure of which is hereby incorporated by reference.

TECHNICAL FIELD

The present invention relates to a patient implant alignment system, in particular for alignment of a patient implant during a surgical procedure. The invention further relates to a method of aligning a patient implant during a surgical procedure.

BACKGROUND

Deterioration or damage to the bones or joints of a human can often only be fixed using surgical means, and is therefore traumatic to the patient. It is therefore less than ideal when surgical procedures are not performed in a desirable manner, as the only means to rectify mistakes is generally by resorting to another operation.

As such, it is critical that the positioning and alignment of surgical implants is correct following the initial surgical procedure, not only so as to ensure correct functioning of the surgical implant, but also to avoid discomfort or restriction to movement for the patient. For example, incorrect alignment of an acetabular cup during hip arthroplasty can prevent the patient from experiencing their previous range of leg movement, diminishing their post-operative quality of life.

To correct incorrectly positioned or aligned patient implants requires a further surgical procedure, which not only causes further trauma to the patient, who may already be in a weakened state from the original operation, but also exposes them to a greater risk of infection. Further surgical procedures also place a greater strain upon the operational capacity of hospitals.

To ensure correct positioning and alignment of patient implants, surgeons will typically utilise guide implants, guiding tools, or other means of indicating the correct alignment. However, such tools are generally quite cumbersome, and can therefore prolong an operation, resulting in fatigue to both surgeon and patient, or can alternatively impede an effective surgical procedure by blocking the surgeon's access to the operative area of the patient. Such tools are also likely to require separate initial alignment themselves, thereby creating a greater workload during the surgery.

SUMMARY

It is therefore an object of the present invention to provide a simplified means of correctly aligning a patient implant to thereby obviate the above-mentioned problems.

According to a first aspect of the invention there is provided a patient implant alignment system, preferably for assisting the operative alignment of a patient implant during a surgical procedure, the system comprising: a patient-reference imaging apparatus capable of imaging an operative area of the patient; a patient implant to be operatively aligned during the surgical procedure; and an augmented display apparatus capable of displaying a virtual overlay of a digital implant model of the patient implant during the surgical procedure to which a surgeon may align the patient implant during the surgical procedure.

Traditional guide tools for aligning surgical implants require significant expenditure of time and effort to correctly align or setup, and the tools must be subsequently removed. By providing a system which enables an augmented virtual environment to be created to enable the surgeon to visually overlap the genuine patient implant with a correctly aligned virtual overlay on a display screen, the alignment of patient implants can be greatly simplified.

By providing an apparatus for imaging an operative area of the patient, reference points of the patient can be taken. The augmented display apparatus may then receive these reference points when displaying the virtual overlay of the patient implant to the surgeon, and the virtual overlay can be displayed in the correct alignment. As such, the surgical alignment of the patient implant can be readily matched to the virtual overlay to ensure correct alignment of the patient implant in vivo.

Preferably, the patient-reference imaging apparatus may include a patient imaging device and at least one indicative marker operatively insertable into the operative area of the patient, the or each indicative marker being detectable by the patient imaging device to determine at least one reference point relating to the operative area. The at least one indicative marker may include a patient-specific implant guide, and the patient imaging device may be an optical image capture device.

Whilst it may be preferable for the patient-reference imaging apparatus to automatically detect the operative area of the patient purely based on captured images, in practice, the patient reference points may well need to be calibrated prior to insertion of the patient implant. Some form of patient-specific implant guide, having indicative markers recognisable by an optical image capture device may therefore simplify the referencing of the operative area of the patient, reducing the length of the surgical procedure, and thereby reducing the possibility of mistakes occurring.

The augmented display apparatus may beneficially be a personal computer, and said personal computer may further include at least part of the patient-reference imaging apparatus.

By providing a personal computer, such as a tablet computer, the image-capture requirements of the patient-reference imaging apparatus and the real-time image display requirements of the augmented display apparatus can be combined into a single device, simplifying the operation for the surgeon.

According to a second aspect of the invention, there is provided a method of aligning a patient implant, the method comprising the steps of: a] generating a digital implant model of the patient implant; b] determining a desired alignment of the patient implant based on predetermined alignment data; c] imaging an operative area of the patient to create patient-specific implant reference data; d] creating a virtual overlay of the digital implant model in the determined desired alignment relative to the patient-specific implant reference data; and e] operatively aligning the patient implant using the virtual overlay.

By providing a process which is capable of assisting the alignment of a patient implant during a surgical procedure, the duration of the surgical procedure can beneficially be reduced, whilst also advantageously improving the accuracy of the alignment of the implant, thereby improving the post-surgery quality of life for the patient.

If a digital implant model of the patient implant is created prior to the surgical procedure being performed, and the desired alignment thereof determined, much of the challenging optimisation of the implant alignment can be performed computationally, ensuring that the patient implant is inserted in such a manner so as to minimise the risk of requiring a further surgical procedure to correct the patient implant position.

Furthermore, by providing a virtual overlay of the digital implant model during the surgical procedure, the surgeon can align the real patient implant to the virtual overlay, which thereby reduces the complexity of the implant alignment process, resulting in fewer errors and therefore a better post-surgery quality of life for the patient.

The predetermined alignment data may preferably include patient-specific data, which may be derived from imaging the operative area of the patient prior to surgery.

Patient-specific data may be taken by imaging the operative area of the patient prior to surgery. This may advantageously permit the person determining the optimum alignment to correct for any abnormalities, providing the patient with as realistic an implant alignment as possible.

The predetermined alignment data may be indicative of one or more post-implant desired activities, and/or one or more dynamic patient characteristics.

The alignment data may additionally or alternatively be taken so as to account for the range of motion that a patient may post-operatively hope to attain, and may relate to one or more post-implant desired activities, such as the ability to play a particular sport, for example. It may therefore be highly advantageous to accrue dynamic patient-specific information, showing the operative region in a state of kinesis.

Preferably, the predetermined alignment data may include patient library data.

Whilst bespoke patient-specific data may be appropriate in some circumstances, it may alternatively be simpler to determine the alignment data from patient library data, thereby accounting for the normal alignment taken from the general population, or a specific population sub-set.

In a preferable embodiment, the method may further comprise a step subsequent to step c] of positively accepting the patient-specific implant reference data, which may be performed automatically, or may be performed by a surgeon.

In order to ensure that the patient-specific implant reference data has been correctly determined by a patient-reference imaging apparatus, it may be wise to positively accept the data determined prior to proceeding with the alignment of the patient implant. This may be performed manually, using the expertise of the surgeon, or automatically, thereby reducing the workload on the surgeon during the surgical procedure.

Preferably, during step d] the virtual overlay of the digital implant model may be displayed in real-time.

Providing a real-time display of the operative area of the patient advantageously allows the surgeon inserting the patient implant to rapidly align the patient implant to the virtual overlay, accelerating the alignment process.

During step c], the imaging of the operative area may utilise an optical imaging device, and said optical imaging device may detect at least one indicative marker operatively inserted into the operative area of the patient.

Recognition of indicative markers placed within the operative area of the patient can advantageously assist the alignment of the virtual overlay, since such recognition can be computationally assisted for speed.

In a preferable embodiment, the patient implant may be an orthopaedic implant.

The invention is most readily applicable to the implant of patient implants to replace osseous or cartilaginous tissue, since such implants must be correctly aligned in order for the musculoskeletal system to function adequately.

According to a third aspect of the invention, there is provided a method of operatively aligning a patient orthopaedic implant, the method comprising the steps of: a] creating the patient orthopaedic implant based on patient-specific data; b] using a computer, generating a digital implant model of the patient orthopaedic implant; c] determining a desired alignment of the patient implant based on predetermined patient-specific dynamic and/or kinematic alignment data; d] imaging an operative area of the patient to create patient-specific implant reference data; e] using a computer, generating a digital model of the patient operative area based on the patient-specific implant reference data; f] using a computer, rendering a virtual overlay of the digital implant model in the digital model of the patient operative area; g] positioning the virtual overlay so as to be visible to a surgeon, and such that the digital model of the patient operative area is in alignment with the patient operative area; and h] the surgeon operatively aligning the patient implant using the virtual overlay.

BRIEF DESCRIPTION OF FIGURES

The invention will now be more particularly described, by way of example only, with reference to the accompanying drawings, in which:

FIG. 6 shows a pictorial representation of the imaging of an operative area of a patient to create patient-specific implant reference data, in accordance with the method shown in FIG. 2; and FIG. 7 shows a pictorial representation of a surgeon implanting and aligning a patient implant, in accordance with the method shown in FIG. 2.

DETAILED DESCRIPTION

Figure 1:
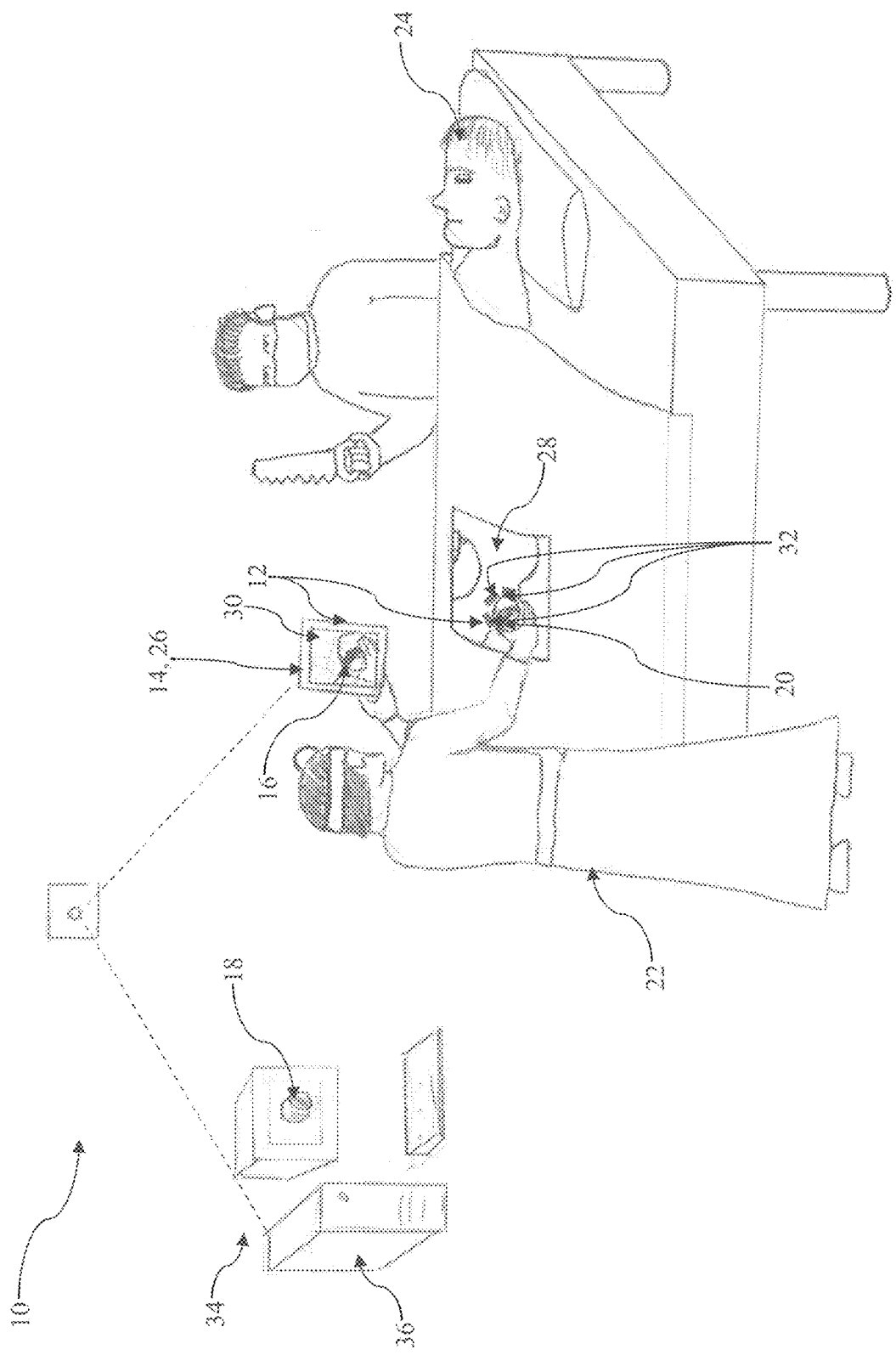
FIG. 1 shows a pictorial representation of one embodiment of a system for assisting the operative alignment of a patient implant during surgery, in accordance with the first aspect of the invention.

Referring firstly to FIG. 1, there is shown a system for assisting the operative alignment of a patient implant during surgery, indicated globally at 10. The system 10 comprises a patient-reference imaging apparatus 12 and an augmented display apparatus 14 which is capable of displaying a virtual overlay 16 of a digital implant model 18 of the patient implant 20 to a surgeon 22 performing a surgical procedure on a patient 24.

The surgical procedure illustrated is the arthroplasty of the patient's acetabulum, although this procedure is shown for illustrative purposes only and it will be appreciated that the invention could readily be applied to any surgical implant procedure.

The patient-reference imaging apparatus 12 and augmented display apparatus 14 are, in the depicted embodiment, both formed as a tablet computing device 26 having an optical imaging device, such as a camera. Critically, whilst the patient-reference imaging apparatus 12 need only be capable of recording still images of an operative area 28 of the patient 24, the augmented display apparatus 14 needs to be able to display real-time images to the surgeon via a display screen 30, and therefore, the two apparatuses 12, 14 could easily be separate devices.

In the depicted embodiment, the patient-reference imaging apparatus 12 comprises a patient imaging device, here the camera of the tablet computing device 26, and preferably at least one indicative marker 32 which is inserted into the operative area 28 of the patient 24. In FIG. 1, this is illustrated as a plurality if infra-red reflectors positioned on the pelvic bone of the patient 24.

The digital implant model 18 is generated from patient specific information on a, preferably remote, computer 34 having a sufficiently powerful processor 36, and the digital implant model 18 can then be transferred to the augmented display apparatus 14, wherein the virtual overlay 16 can be generated and displayed.

To use the system 10, a surgeon 22 uses the patient-reference imaging apparatus 12 to determine reference points of an operative area 28 of the patient 24, such that the virtual overlay 16 can be aligned into a desired alignment and displayed to the surgeon 22 in real-time on the augmented display apparatus 14. The reference points are determined between the patient imaging device 26 and the indicative markers 32, although such referencing and subsequent registering could be performed automatically by the computer and/or manually by the surgeon 22.

The augmented display apparatus 14 will display the digital implant model 18 in a desired predetermined alignment as the virtual overlay 16 on a display screen 30 of the augmented display apparatus 14, having utilised the reference points of the operative area 28 to ensure that the virtual overlay 16 is displayed to the surgeon 22 in the correct orientation during the operation.

The augmented display apparatus 14 displays real-time images of the operative area 28 of the patient 24 via its display screen 30, and therefore the surgeon 22 can see themselves align the patient implant 20 in vivo. By matching the position of the patient implant 20 on the display screen 30 to that shown by the virtual overlay 16, the surgeon 22 can align the patient implant 20 without the need for any cumbersome guiding tools mid-operation.

Figure 2:
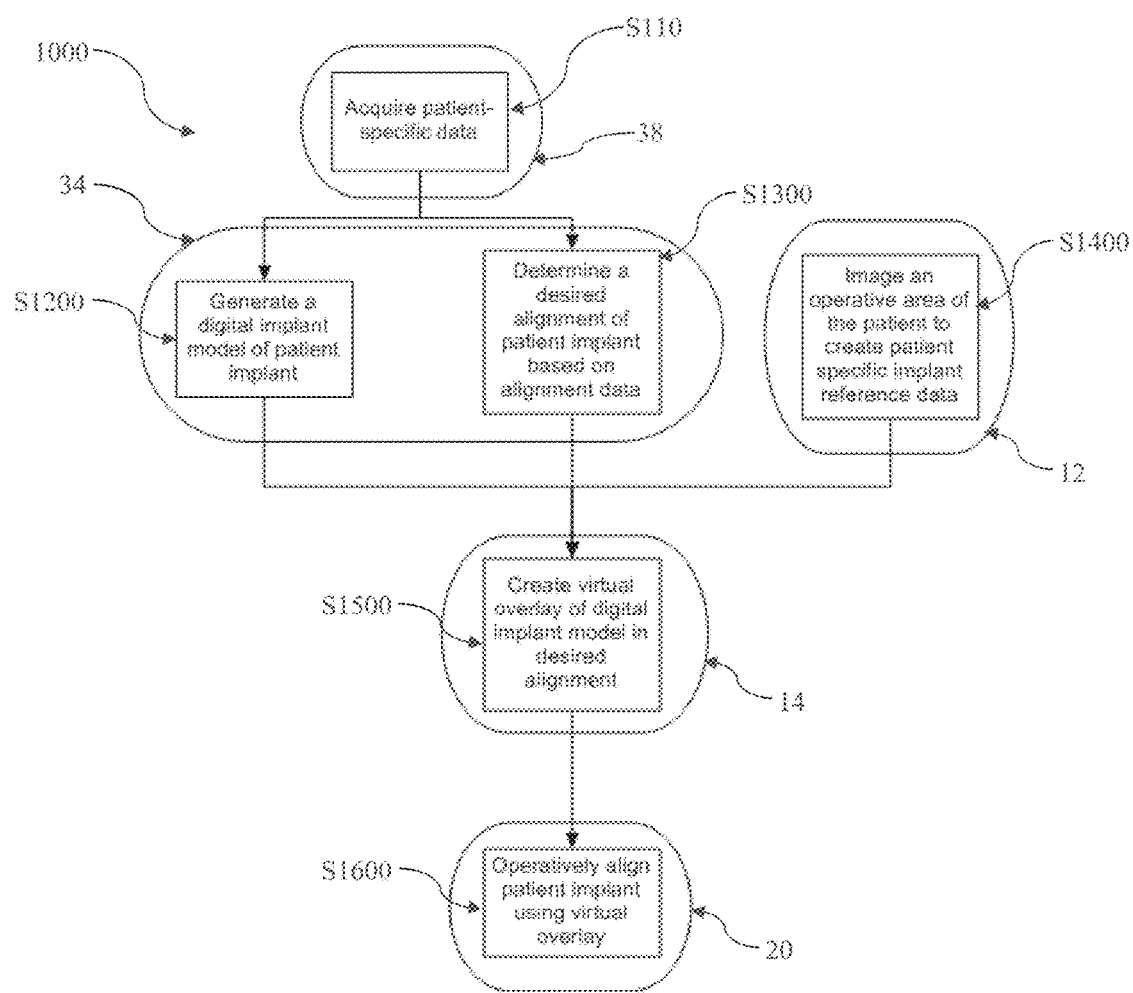
FIG. 2 shows a diagrammatic representation of a method of aligning a patient implant in accordance with the second aspect of the invention.

The above-described system merely gives a summary of the equipment necessary to effect the present invention during a surgical procedure. Hereafter follows a more detailed description of the steps required in a method of aligning a patient implant. The method is shown in summary in FIG. 2, indicated generally at 1000.

Firstly, data specific to the patient should be acquired at step S1100 such that the digital implant model 18 can be generated based on real data, and also such that the desired patient implant alignment can be determined. Patient-specific data can be acquired using various patient interrogation means, but will hereafter be illustrated by using an X-Ray scanner 38 to interrogate the operative area 28 of the patient 24. It will be clear however, that other or additional means of interrogation are possible, such as CT and/or MRI scanning of the operative area 28.

However, whilst patient-specific data is preferably used, it will be appreciated that patient-independent alignment data could be used, such as patient library data which correlates to average healthy alignments in the general population.

Based on the determined alignment data, the digital implant model 18 of the patient implant 20 can be generated computationally at step S1200. This would generally be performed prior to the surgical procedure on the or a separate computer 34, but with the exponential increase in computational power over time, it is feasible that this could be performed in situ by the patient-reference imaging apparatus 12 or augmented display apparatus 14.

The digital model 18 is created as a virtual replica of the patient implant 20 and/or implant area. This may be achieved by, for example, imaging a plurality of reference points of the operative area 28 and then performing mathematical analysis to generate a three-dimensional model thereof, using finite element analysis, for instance, to generate a three-dimensional mesh model. Other rendering software could be used as an alternative, of course.

The desired alignment of the patient implant 20 is also determined at step S1300 based on, preferably patient-specific, alignment data. This could be based on a predetermined average from the general population, or may be based on patient-specific kinematic data or dynamic patient characteristics.

Figure 3:
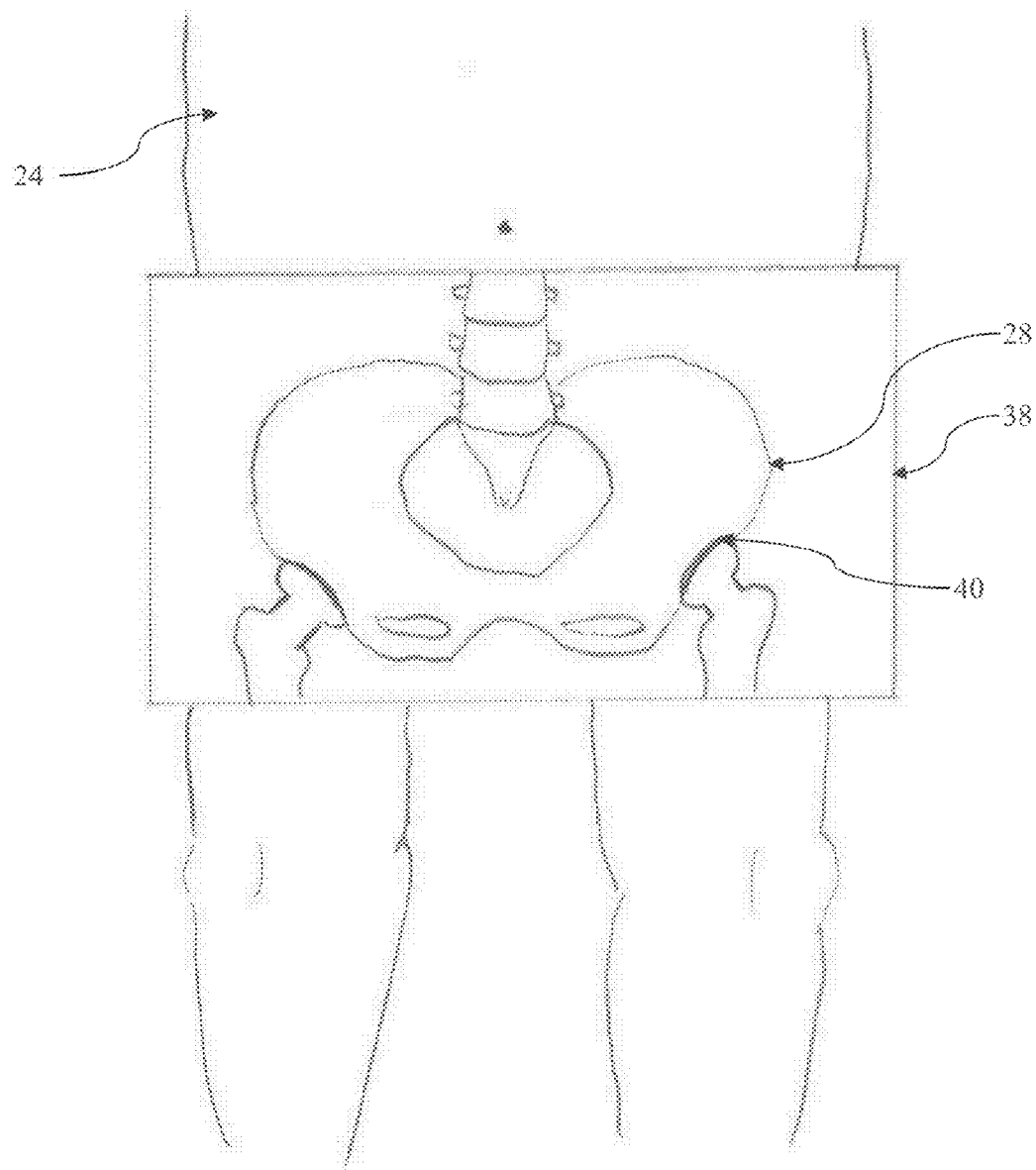
FIG. 3 shows a pictorial anterior representation of a patient being scanned to acquire patient-specific data, in accordance with the method shown in FIG. 2.
Figure 4:
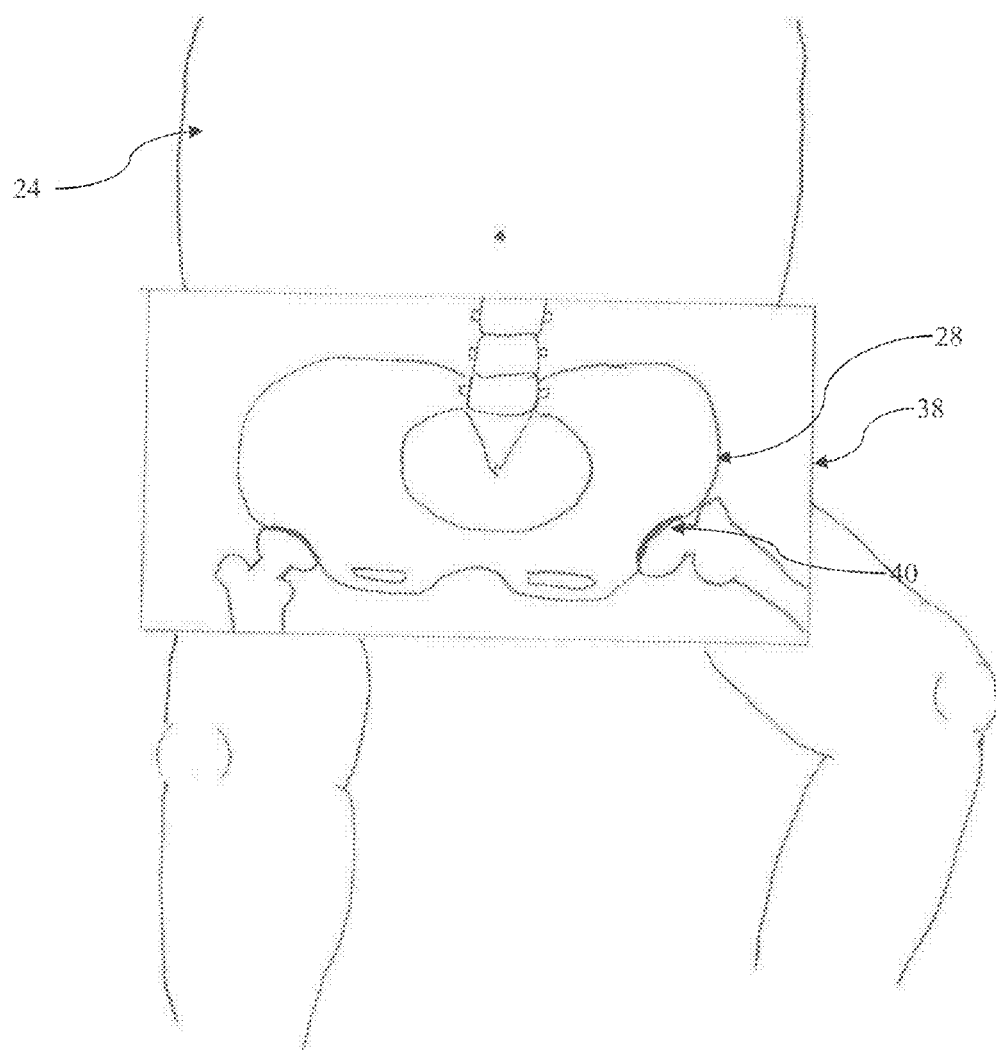
FIG. 4 shows the patient of FIG. 3 in an alternative kinematic position.
Figure 5:
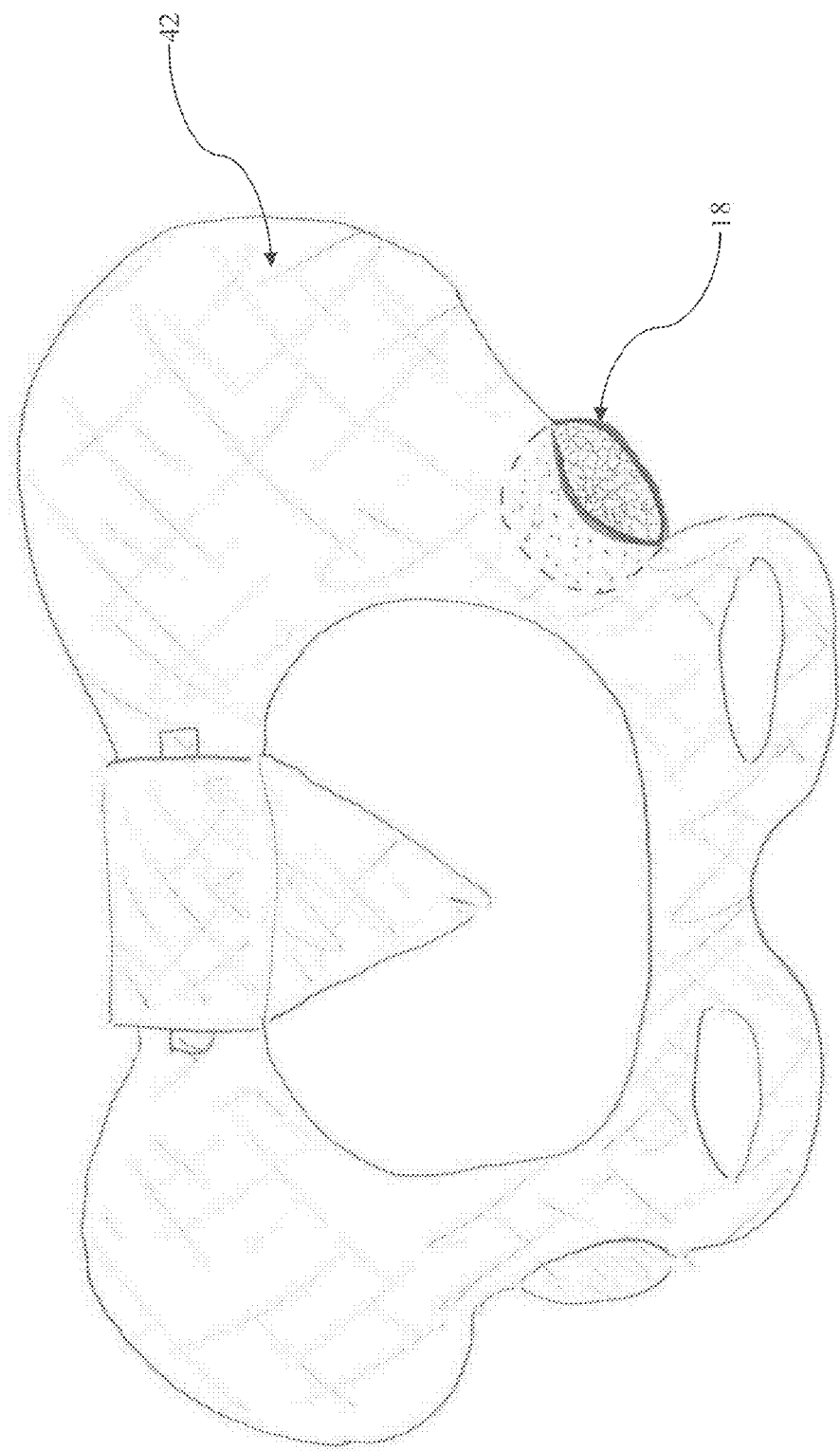
FIG. 5 shows a pictorial anterior representation of a digital implant model created in accordance with the method shown in FIG. 2.

The creation of the digital implant model 18 is critical, as this allows for the correct alignment of a patient implant 20 to be determined prior to surgery. The creation of the digital implant model 18 is shown in FIGS. 3 to 5. FIG. 3 shows the patient 24 in a standing position behind, for example, an X-Ray scanner 38 so as to image the pelvic region, in particular, the acetabulum 40. The processor 36 of the computer 34 is capable of processing the resultant X-Ray images, which can be analysed and converted into the digital implant model 18.

Although the surface structure of the patient implant 20 is most relevant for the creation of the digital implant model 18, and this can be readily gleaned from X-Ray imaging, it will be appreciated that more sophisticated patient scanning is available, such as CT scanning, which may allow for secondary data relating to the patient 24 to be recorded, such as bone density information. This then permits the digital implant model 18 to be tailored based upon such information.

Whilst static scanning yields the necessary structural information about the patient 24, no dynamic or kinematic data is registered. However, as shown in FIG. 4, the patient 24 can be imaged in a variety of dynamic and/or kinematic positions, showing the alignment of their acetabulum 40, giving an indication of the range of motion of the joint for the patient 24. The surgeon 22 and/or analyst can then determine an optimum or otherwise desirable alignment in which a replacement patient implant 20, such as an acetabular cup, may be positioned in vivo. The desired alignment may be determined based on any number of factors, for instance: maximised post-operative mobility and/or dexterity; a range of motion which is indicative of one or more post-implant activities; and/or ease of surgical implant.

Once the digital implant model 18 and the desired patient implant alignment have both been determined, a fully realised model of the operative area 28, shown in FIG. 5 as a digital model of the pelvis 42 and a digital model of an acetabular cup implant 18, is generated. By fully realising a digital model of the entire operative area 28, it is possible to orient and align the respective digital models 18, 42 relative to one another, and computationally determine how the desired patient implant 20 alignment would likely be realised during an operation. As such, this relative alignment can be stored for use in the subsequent generation of the virtual overlay 16. The creation of the digital implant model 18 therefore concludes the pre-operative portion of the procedure.

During a surgical procedure, the surgeon 22 needs to create a correspondence between the digital implant model 18 and the operative area 28 of the patient 24, and this is achieved by using the patient-reference imaging apparatus 12 to image the operative area 28 (step S1400 in FIG. 2) to create patient-specific implant reference data. This may be achieved by creating sufficient reference points to determine how the acetabulum 40 of the patient corresponds with the digital model of the pelvis 42, allowing the digital model 18 of the implant to be virtually aligned.

This could feasibly be achieved by using an optical imaging device such as a tablet computing device 26 and directly imaging the operative area of the patient 28, using automatic recognition software of the tablet computing device 26 to determine what part of the patient 24 is being imaged.

However, and as shown in FIG. 6, given that it is critical to correctly identify the operative area 28 of the patient, it is preferable to provide a plurality of indicative markers 32 which are easily recognised by a processor associated with the patient-reference imaging apparatus 12. There may also be provided a secondary fail-safe to recognition of the operative area 28 by requiring the surgeon 22 to positively accept the or each image taken by the patient-reference imaging apparatus 12 before proceeding. This also has the added benefit of ensuring that a surgical procedure, in which the patient may be under anaesthetic and internally exposed, is not delayed whilst computational processing occurs.

The indicative markers 32 may, as illustrated, be provided so as to be physically attached onto, for example, bone in the operative area 28 of the patient. However, a guide implant, similar in shape and form to the patient implant 20 may be formed in addition or as an alternative, which the surgeon 22 may insert into the operative area 28 which may also carry a plurality of recognisable markers. Such markers 32 could, for example, be formed as infra-red reflectors, which are readily detectable and identifiable.

Once a reference for the digital implant model 18 has been created by imaging in step S1400 the operative area 28 of the patient 24, the augmented display apparatus 14 may be provided. If the real-time image-capture portion of the augmented display apparatus 14 is aimed so as to image the operative area 28 of the patient 24 in real-time as a video feed, then the surgeon 22 can view the operative area 28 via the display screen 30 of the augmented display apparatus 14. Such an arrangement is shown in FIG. 7.

The digital implant model 18 is transmitted to the augmented display apparatus 14, from which is created the virtual overlay 16 in step S1500. This virtual overlay 16 may be displayed as a three-dimensional structure in the live display shown on the display screen 30, preferably being at least in part transparent or translucent so as not to obscure the in-progress operation.

Utilising the determined reference points, the virtual overlay 16 can be displayed in what would be the correct alignment for the patient implant 20 once inserted. The surgeon 22 can therefore visualise both the position of the patient implant 20 as they insert it into the patient 24, whilst also being able to visualise the target alignment as shown by the virtual overlay 16. In step S1600, by matching the patient implant 20 position with that illustrated by the virtual overlay 16, the surgeon 22 can be certain that their implant has been successfully aligned.

Whilst the virtual overlay 16 is shown as just an overlay of the digital model 18 of an acetabular cup, it will be readily apparent that any digitised portion of the operative area 28 could feasibly be overlain on the augmented display apparatus 14 so as to assist the surgeon 22 during the surgical procedure.

It will be appreciated that although hip arthroplasty has been used in an exemplary manner to describe the invention, any surgical procedure could feasibly utilise the system and method described, invasive or otherwise. The invention is anticipated to be primarily useful in situations in which bone is replaced during an operation, such as knee or ankle reconstruction, but it could also feasibly be utilised in the replacement of non-osseous tissue, for example, in plastic surgery.

It is therefore possible to provide a patient implant alignment system which allows a surgeon to display a virtual overlay of a patient implant to be inserted during a surgical procedure on a display device. The virtual overlay can be made to be visible in real-time, allowing the surgeon to use the overlay as a reference to correctly align the implant in the patient. In doing so, the need for cumbersome guide tools is removed, simplifying the already complicated surgical procedure by using an augmented reality surgical environment.

The words 'comprises/comprising' and the words 'having/including' when used herein with reference to the present invention are used to specify the presence of stated features, integers, steps or components, but do not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

The embodiments described above are provided by way of examples only, and various other modifications will be apparent to persons skilled in the field without departing from the scope of the invention herein described and defined.

What is claimed is:

1. A patient implant alignment system, the system comprising:
   an optical imaging device capable of imaging an operative area of the patient;
   at least one indicative marker configured to be insertable into and directly attachable to the operative area of the patient, the at least one indicative marker being detectable by the optical imaging device;
   a patient implant to be operatively aligned during a surgical procedure;
   a digital implant model of the patient implant; and
   an augmented display apparatus comprising the optical imaging device, the augmented display apparatus being capable of aligning and displaying a virtual overlay of the digital implant model of the patient implant in a real-time image of the operative area captured by the optical imaging device during the surgical procedure, wherein the aligned virtual overlay is in a predetermined alignment based on at least one reference point of the operative area so that the virtual overlay is correctly oriented with respect to the operative area of the patient, and to which a surgeon may align the patient implant during the surgical procedure, wherein the at least one reference point of the operative area is generated responsive to the at least one indicative marker.

2. The patient implant system as claimed in claim 1, wherein the at least one indicative marker includes a patient-specific implant guide.

3. The patient implant system as claimed in claim 1, wherein the augmented display apparatus is a personal computer.

4. The patient implant alignment system as claimed in claim 1, wherein the at least one indicative marker comprises a plurality of independently attachable indicative markers.

5. The patient implant alignment system as claimed in claim 1, wherein the at least one indicative marker is configured to be attachable directly to a bone comprised in the operative area of the patient.

6. The patient implant alignment system as claimed in claim 1, wherein the optical imaging device is capable of directly intraoperatively imaging the operative area of the patient.

7. The patient implant alignment system as claimed in claim 1, wherein the at least one indicative marker comprises an infra-red reflector.

8. A method of aligning a patient implant, the method comprising the steps of:
   a] generating a digital implant model of the patient implant;
   b] determining a desired alignment of the patient implant based on predetermined alignment data;
   c] imaging with an optical imaging device an operative area of the patient having at least one indicative marker inserted into and attached directly to the operative area;
   d] generating at least one reference point of the operative area responsive to the at least one indicative marker;
   e] utilizing the at least one reference point of the operative area to determine how the operative area corresponds with the digital implant model, to create patient-specific implant reference data;
   f] creating a virtual overlay of the digital implant model in the determined desired alignment relative to the patient-specific implant reference data, and displaying in an augmented display apparatus the virtual overlay in a real-time image of the operative area captured by the optical imaging device such that the virtual overlay is correctly orientated with respective to the operative area, wherein the optical imaging device is comprised in the augmented display apparatus; and
   g] operatively aligning the patient implant using the virtual overlay.

9. The method as claimed in claim 8, wherein the predetermined alignment data includes patient-specific data.

10. The method as claimed in claim 9, wherein the patient-specific data is derived from imaging the operative area of the patient prior to surgery.

11. The method as claimed in claim 8, wherein the predetermined alignment data is indicative of one or more post-implant desired activities.

12. The method as claimed in claim 8, wherein the patient-specific data is indicative of one or more dynamic patient characteristics.

13. The method as claimed in claim 8, wherein the predetermined alignment data includes patient library data.

14. The method as claimed in claim 8, further comprising a step subsequent to step e] of positively accepting the patient-specific implant reference data.

15. The method as claimed in claim 14, wherein the positive acceptance of the patient-specific implant reference data is performed automatically.

16. The method as claimed in claim 14, wherein the positive acceptance of the patient-specific implant reference data is performed by a surgeon.

17. The method as claimed in claim 8, wherein the optical imaging device detects the at least one indicative marker operatively inserted into the operative area of the patient.

18. The method as claimed in claim 8, wherein the patient implant is an orthopaedic implant.

19. A method of operatively aligning a patient orthopaedic implant, the method comprising the steps of:
   a] creating the patient orthopaedic implant based on patient-specific data;
   b] using a computer, generating a digital implant model of the patient orthopaedic implant;
   c] determining a desired alignment of the patient implant based on predetermined patient-specific dynamic and/or kinematic alignment data;
   d] imaging with an optical imaging device an operative area of the patient having at least one indicative marker inserted into and attached directly to the operative area and generating at least one reference point of the operative area responsive to the at least one indicative marker, to create patient-specific implant reference data;
   e] using a computer, generating a digital model of the patient operative area based on the patient-specific implant reference data, utilizing the at least one reference point of the operative area to determine how the operative area corresponds with the digital model of the patient operative area;
   f] using a computer, rendering a virtual overlay of the digital implant model in the digital model of the patient operative area;
   g] positioning an augmented display apparatus comprising the optical imaging device so as to be visible to a surgeon, and displaying the virtual overlay in the augmented display apparatus such that the digital model of the patient operative area is in alignment with a real-time image of the patient operative area as captured by the optical imaging device; and
   h] the surgeon operatively aligning the patient implant using the virtual overlay.

* * * * *